United States Patent
Benson et al.

(10) Patent No.: US 8,653,461 B1
(45) Date of Patent: *Feb. 18, 2014

(54) THERMOGRAPHY CAMERA TUNED TO DETECT ABSORPTION OF INFRARED RADIATION IN A SELECTED SPECTRAL BANDWIDTH

(75) Inventors: Robert G. Benson, New Ipswich, NH (US); Thomas J. Scanlon, Hampstead, NH (US); Paul A. Czerepuszko, Hopkinton, MA (US)

(73) Assignee: FLIR Systems, Inc., Wilsonville, OR (US)

( * ) Notice: Subject to any disclaimer, the term of this patent is extended or adjusted under 35 U.S.C. 154(b) by 297 days.

This patent is subject to a terminal disclaimer.

(21) Appl. No.: 12/415,721

(22) Filed: Mar. 31, 2009

Related U.S. Application Data (63) Continuation-in-part of application No. 11/726,918, filed on Mar. 23, 2007.

(51) Int. Cl.
 *G01N 21/35* (2006.01)
(52) U.S. Cl.
 USPC .................................. 250/339.01; 250/338.4
(58) Field of Classification Search
 USPC ....................... 250/338.1, 338.4, 339.01, 332
 See application file for complete search history.

(56) References Cited

U.S. PATENT DOCUMENTS

| | | | |
|---|---|---|---|
| 3,662,171 A | 5/1972 | Brengman et al. | |
| 4,390,785 A | 6/1983 | Faulhaber et al. | |
| 4,496,840 A | 1/1985 | Fabinski et al. | |
| 4,520,265 A | 5/1985 | Griggs et al. | |
| 4,535,639 A | 8/1985 | Bianchini | |
| 4,543,481 A | 9/1985 | Zwick | |
| 4,555,627 A | 11/1985 | McRae, Jr. | |
| 4,745,276 A | 5/1988 | Broicher et al. | |
| 4,772,789 A * | 9/1988 | Maram et al. | 250/330 |
| 4,871,916 A | 10/1989 | Scott | |
| 4,894,526 A | 1/1990 | Bethea et al. | |
| 5,001,346 A | 3/1991 | Barkhoudarian | |

(Continued)

FOREIGN PATENT DOCUMENTS

WO  WO 2005001409 A2 *  1/2005

OTHER PUBLICATIONS

Brochure, Sherlock "Remote gas leak imaging and qualification", published by Gas Imaging Technology, Buellton, CA, USA, no date (www.gitint.com).

(Continued)

*Primary Examiner* — Casey Bryant
(74) *Attorney, Agent, or Firm* — Haynes and Boone, LLP (57) ABSTRACT

An infrared camera system is provided to detect absorption of infrared radiation in a selected spectral bandwidth. In one example, an infrared camera system includes a lens adapted to receive infrared radiation from a survey scene comprising one or more gasses. The infrared camera system also includes a focal plane array comprising a plurality of quantum well infrared photo detectors (QWIPs). The QWIPs are tuned to detect a limited spectral bandwidth of the infrared radiation corresponding to at least a portion of an infrared absorption band of the one or more gasses. The infrared camera system also includes an optical band pass filter positioned substantially between the lens and the focal plane array. The optical band pass filter is adapted to filter the infrared radiation to a wavelength range substantially corresponding to the limited spectral bandwidth of the QWIPs before the infrared radiation is received by the focal plane array.

19 Claims, 4 Drawing Sheets

(56) References Cited

U.S. PATENT DOCUMENTS

| | | | |
|---|---|---|---|
| 5,023,685 A | 6/1991 | Bethea et al. | |
| 5,161,408 A | 11/1992 | McRae et al. | |
| 5,225,679 A | 7/1993 | Clarke et al. | |
| 5,255,073 A | 10/1993 | Wallin et al. | |
| 5,264,368 A | 11/1993 | Clarke et al. | |
| 5,317,897 A | 6/1994 | Jellye et al. | |
| 5,386,117 A | 1/1995 | Piety et al. | |
| 5,430,293 A | 7/1995 | Sato et al. | |
| 5,479,258 A | 12/1995 | Hinnrichs et al. | |
| 5,523,569 A | 6/1996 | Hornfeld et al. | |
| 5,637,871 A | 6/1997 | Piety et al. | |
| 5,656,813 A | 8/1997 | Moore et al. | |
| 5,661,590 A | 8/1997 | Almogy et al. | |
| 5,780,724 A | 7/1998 | Olender et al. | |
| 5,824,884 A | 10/1998 | Ollender et al. | |
| 5,834,632 A | 11/1998 | Olender et al. | |
| 5,854,422 A | 12/1998 | McKeon et al. | |
| 5,866,073 A | 2/1999 | Sausa et al. | |
| 5,867,264 A | 2/1999 | Hinnrichs | |
| 5,965,899 A | 10/1999 | Little et al. | |
| 6,089,076 A | 7/2000 | Mueller et al. | |
| 6,154,307 A | 11/2000 | Veronesi et al. | |
| 6,157,033 A | 12/2000 | Chudnovsky | |
| 6,327,896 B1 | 12/2001 | Veronesi et al. | |
| 6,355,939 B1 | 3/2002 | Dodd | |
| 6,642,537 B1 | 11/2003 | Gunapala et al. | |
| 6,657,195 B1 | 12/2003 | Martin et al. | |
| 6,680,778 B2 | 1/2004 | Hinnrichs et al. | |
| 6,690,472 B2 | 2/2004 | Kulp et al. | |
| 6,734,452 B2 | 5/2004 | Gunapala et al. | |
| 6,803,577 B2 | 10/2004 | Edner et al. | |
| 6,822,742 B1 | 11/2004 | Kalayeh et al. | |
| 6,866,089 B2 | 3/2005 | Avila | |
| 6,885,965 B2 | 4/2005 | Butler et al. | |
| 6,995,846 B2 | 2/2006 | Kalayeh et al. | |
| 7,022,993 B1 | 4/2006 | Williams, II et al. | |
| 7,030,381 B2 | 4/2006 | Kilian et al. | |
| 7,075,653 B1 | 7/2006 | Rutherford | |
| 7,134,322 B1 | 11/2006 | Baird | |
| 7,151,787 B2 | 12/2006 | Kulp et al. | |
| 7,649,174 B2 | 1/2010 | Mammen et al. | |
| 7,679,046 B1* | 3/2010 | Benson et al. | 250/252.1 |
| 2002/0074542 A1* | 6/2002 | Gunapala et al. | 257/14 |
| 2002/0098592 A1* | 7/2002 | Neilson et al. | 436/147 |
| 2002/0098593 A1* | 7/2002 | Nelson et al. | 436/147 |
| 2002/0132360 A1* | 9/2002 | Neilson et al. | 436/147 |
| 2002/0146836 A1* | 10/2002 | Neilson et al. | 436/147 |
| 2003/0025081 A1* | 2/2003 | Edner et al. | 250/339.09 |
| 2004/0108564 A1* | 6/2004 | Mitra | 257/442 |
| 2005/0017176 A1* | 1/2005 | Koch et al. | 250/338.4 |
| 2005/0082520 A1 | 4/2005 | Fathimulla et al. | |
| 2006/0049352 A1 | 3/2006 | Irani | |
| 2006/0091310 A1* | 5/2006 | Furry | 250/330 |
| 2008/0231719 A1* | 9/2008 | Benson et al. | 348/222.1 |
| 2009/0200466 A1* | 8/2009 | Mammen et al. | 250/330 |
| 2010/0231722 A1* | 9/2010 | Hill et al. | 348/164 |

OTHER PUBLICATIONS

Valenti, Spotting substation gas leaks, Mechanical Engineering, May 2000, pp. 18-22, 29-31, (http://www.memagazine.org/supparch/mepower00/gas/gas.html).

Brochure, Ion Science "SF6 Gascheck P1", published by Ion Science, Cambridge, UK, no date, (www.ionscience.com).

User Manual (related pages); ThermaCam GasFind IR published by FLIR Systems, Inc., North Billerica, MA, USA, publication No. 230438-000, Rev B, issue date Jul. 14, 2006.

Wimmers et al., Focal Plane Arrays: Better, Smaller IR Imagers for New Applications, The Photonics Design and Applications Handbook, H-212-217, 1997.

Wimmers et al., "Better, Smaller IR Imagers Lead the Way to New Applications", Photonics Spectra, Dec. 1994, pp. 113-118.

* cited by examiner

THERMOGRAPHY CAMERA TUNED TO DETECT ABSORPTION OF INFRARED RADIATION IN A SELECTED SPECTRAL BANDWIDTH

CROSS-REFERENCE TO RELATED APPLICATIONS

This patent application is a continuation-in-part patent application of U.S. patent application Ser. No. 11/726,918 filed Mar. 23, 2007, which is incorporated by reference herein in its entirety.

BACKGROUND OF THE INVENTION

1. Technical Field

The invention relates generally to a camera system configured to detect infrared radiation such as, for example, the identification of various substances. More specifically, the invention relates to a camera system configured to detect a limited spectral bandwidth of infrared radiation.

2. Description of the Related Art

"Leak detection and repair" (LDAR) is a common problem in commercial applications where various substances are processed, stored, distributed, and utilized. In the petrochemical industry, leak detection devices include sniffers, scanners and passive imaging devices configured to identify a petrochemical leak by sensing the absorption of infrared radiation by the leaking compound at one or more predetermined infrared absorption bandwidths. In particular, methane ($CH_4$), has strong infrared absorption bands approximately centered at the non-visible wavelengths 1.33 µm, 1.67 µm, 3.3 µm and 7.6 µm, and it is known to construct leak detecting devices to determine if methane is present in a gas sample by determining if the gas sample absorbs radiation at one or more of the methane absorption wavelengths. Similarly, other compounds may be detected by leak detection devices tuned to determine if other compounds are present in a gas sample by determining if the gas sample absorbs radiation at one or more absorption bands associated with the other compounds.

One example of a sniffer device is disclosed in U.S. Pat. No. 7,022,993 to Williams II et al. The sniffer device draws a gas sample into a chamber through a probe, transmits an infrared radiation beam through the gas sample to a photo detector, and a photo detector response signal is used to determine if the gas sample is absorbing infrared radiation at one or more predetermined absorption bands. One problem with using a sniffer device to detect gas leaks is that the probe must take in a gas sample directly from the leak plume in order to detect the leak. Accordingly, in a large facility or along miles of distribution conduits, leak detection by using a sniffer device is often inefficient and unreliable because leaks may be missed. Moreover, a user must be able to place the probe in the leak plume and this may not always be practical.

One example of a scanner device, called a laser methane detector, is disclosed in U.S. Pat. No. 7,075,653 to Rutherford. The laser methane detector scans a survey area with a tunable IR laser diode emitter and analyzes IR radiation reflected back from the survey area to a photo detector. If the presence of a methane plume is detected in the survey area, the laser methane detector alerts an operator by sounding an audible alarm. The tunable IR laser diode emitter is tuned over a range of wavelengths that includes in-band wavelengths, (approximately 1.67 µm), that are absorbed by methane, and out-of-band wavelengths that are not absorbed by methane and to use the photo detector response to determine if methane is present. The laser methane detector provides an advantage over a sniffer because the laser methane detector may detect a methane gas plume from a remote distance. However, one problem with the laser methane detector disclosed by Rutherford is that the tunable IR laser emitter is limited to emitting over a wavelength range of about 1.2-2.5 µm. Accordingly, the laser methane detector is only usable to detect compounds with a strong absorption band within the wavelength range of about 1.2-2.5 µm.

One example of a passive imaging device configured to detect the presence of methane and other hydrocarbon gas plumes is a video thermography camera that includes a lens positioned to form an image of a survey scene that may contain an infrared absorbing gas plume. The image of the survey scene is focused onto a focal plane array and an optical band pass filter is positioned between the lens and the focal plane array to limit the spectral bandwidth of the image of the survey scene to a desired wavelength range. The desired wavelength range corresponds with an absorption band of a compound that it is desired to detect in the image of the survey scene.

The example thermography camera includes a focal plane array that comprises indium antimonide (InSb) IR photo sensor elements. InSb photo sensor elements have a usable responsivity over the approximate spectral range of 1-5.5 µm, but are more practically limited to a usable range of 3.0-5.0 µm. Accordingly, the example thermography camera is practically limited to detecting leak plume containing compounds that have absorption bands in the spectral range of 3.0-5.0 µm. While that range is suitable for detecting methane and other hydrocarbon compound leaks, there is a need for a thermographic leak detector that operates to detect compounds having absorption bands above 5.0 µm.

Another problem with conventional thermographic leak detection systems is that InSb focal plane arrays have a broad spectral responsivity, e.g. 2 µm, as compared to typical absorption bands, which may have a spectral bandwidth of 0.1-0.3 µm. The problem is that the extra spectral responsivity range of the InSb focal plane arrays contributes dark current signal noise that ultimately reduces the contrast of the leak plume as compared to the background of a video survey image. Accordingly, it is desirable to use a photo sensor that has a spectral responsivity range that is spectrally tuned to the absorption bandwidth of the compound to be imaged in order to increase image contrast.

Additionally, in other industries, notably electrical power distribution, there is a need for a thermography camera for detecting leaks of the industrial gas sulfur hexafluoride ($SF_6$). $SF_6$ is commonly used as an electrical insulator and has a strong absorption band at approximately 10.57 µm. Conventional thermography cameras do not have a focal plane array capable of forming an image of a survey scene over a wavelength range that includes 10.57 µm.

There is also a need for a thermography camera for detecting other gasses associated with other particular wavelength ranges. In this regard, the various aspects of conventional thermography cameras described above may similarly limit the ability of such cameras to detect gasses in these other particular wavelength ranges.

BRIEF SUMMARY

One or more embodiments may be used to provide infrared camera systems configured to detect a limited spectral bandwidth of infrared radiation included in an infrared absorption band of one or more substances, such as gasses. Methods relating to the operation, use, and manufacture of such infrared camera systems are provided in other embodiments.

For example, in one embodiment, an infrared camera system includes a lens adapted to receive infrared radiation from a survey scene comprising one or more gasses. The infrared camera system also includes a focal plane array comprising a plurality of quantum well infrared photo detectors (QWIPs). The QWIPs are tuned to detect a limited spectral bandwidth of the infrared radiation corresponding to at least a portion of an infrared absorption band of the one or more gasses. The infrared camera system also includes an optical band pass filter positioned substantially between the lens and the focal plane array. The optical band pass filter is adapted to filter the infrared radiation to a wavelength range substantially corresponding to the limited spectral bandwidth of the QWIPs before the infrared radiation is received by the focal plane array.

In another embodiment, a method of manufacturing an infrared camera system includes selecting a lens adapted to receive infrared radiation from a survey scene comprising one or more gasses. The method also includes forming a plurality of quantum well infrared photo detectors (QWIPs) of a focal plane array such that the QWIPs are tuned to detect a limited spectral bandwidth of the infrared radiation corresponding to at least a portion of an infrared absorption band of the one or more gasses. The method also includes selecting an optical band pass filter adapted to filter the infrared radiation to a wavelength range substantially corresponding to the limited spectral bandwidth of the QWIPs.

Figure 1:
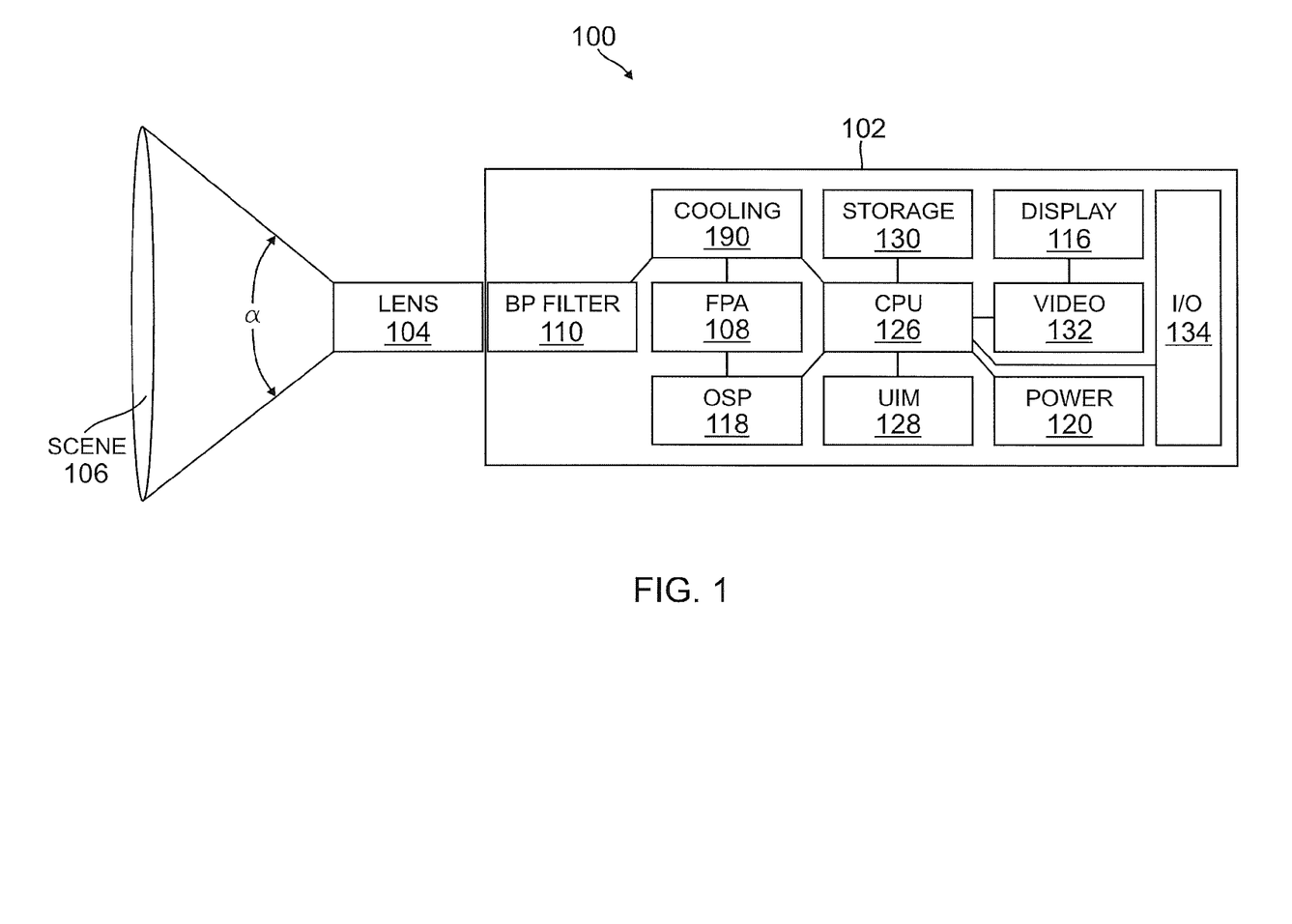
FIG. 1 illustrates a schematic diagram of a camera system in accordance with an embodiment.

In another embodiment, a camera system 100 (e.g., an infrared camera system such as a portable infrared thermography camera) is configured to form a video image of a survey scene 106 over a narrow spectral bandwidth of radiation collected from the scene 106 by a lens 104. In particular, the camera system 100 includes a lens 104 forming an image of the scene 106 onto a focal plane array, (FPA), 108. The FPA 108 may comprise a two dimensional array of photo sensor elements configured with sufficient resolution to form a viewable image of the scene 106 on a display device, e.g. 320×256 photo sensor elements. The photo sensor elements are configured to provide a spectral responsivity profile having a peak responsivity in a desired wavelength range. In one embodiment, the photo sensor elements are configured to provide a wavelength range 10.4 to 10.8 µm and a full width half maximum spectral responsivity bandwidth less than 2.0 µm and preferably less than 0.7 µm. Preferably, the FPA 108 comprises quantum well infrared photo detectors (QWIPs) tuned to the desired spectral responsivity by constructing quantum well layers alternating with barrier layers having appropriate thickness, spacing, impurity doping and other parameters as may be required. Preferably, the quantum well layers comprise gallium arsenide (GaAs) doped with silicon and the barrier layers comprise aluminum gallium arsenide (AlGaAs) but other III-V semiconductor compounds are usable.

The camera system 100 includes an optical band pass filter 110 positioned between the lens 104 the FPA 108 for optically filtering radiation collected by the lens to narrow the spectral bandwidth of the focused image formed on the FPA 108. In one example, the band pass filter 110 has a peak spectral transmittance in the wavelength range 10.30 µm to 10.70 µm and a less than 0.1% of the peak spectral transmittance outside the wavelength range 10.28 µm to 10.72 µm. Other peak spectral transmittance wavelength ranges are also contemplated. In another example, the band pass filter 110 has a full width half maximum transmittance bandwidth of 10.40 to 10.80 µm. Other full width half maximum transmittance bandwidth values are also contemplated. In addition, the camera system 100 includes a refrigeration device configured to cool the FPA 108 and the band pass filter 110 to an operating temperature of less than 65° K.

Generally, the camera system 100 is used for detecting a gaseous compound in the scene 106 when radiation from the scene 106 is received by the lens 104 and passed to the band pass filter 110 to limit the wavelength range of survey scene energy focused onto the FPA 108. In one embodiment, the wavelength range is limited to 10.3 to 10.8 µm. Other wavelength ranges are also contemplated. Each sensor element of the FPA 108 generates an analog photo current value according to a photo current responsivity profile and other factors in response to an irradiance generated by the spectrally filtered scene image formed by the lens 104 at the sensor element active surface. The analog photo current values are read out from each photo sensor element and converted to corresponding digital signal values for rendering a video image frame corresponding to the digital signal values.

The video image frames are formatted for display on a display device 116, e.g. at a standard video rate, for a user to view through an eyepiece 114. Accordingly, a user may point the camera system 100 at the scene 106 that may include a gas leak plume comprising compound having an absorption band while observing the display device 116 to determine if there is a gas leak plume visible on the display device 116. In one embodiment, the absorption band at least partially falls within the wavelength band 10.3 to 10.8 µm. Other wavelength bands are also contemplated.

The camera system 100 is usable to detect an invisible gas plume in a video image of the scene 106 if the gas plume contains a gas that at least partially falls within the wavelength band. In one embodiment, sulfur hexafluoride ($SF_6$), ammonia, ($NH_3$), uranyl fluoride ($U_2O_2F_2$), or any other gas having an absorption band that at least partially falls within the wavelength band 10.3 to 10.8 µm may be detected. Other gasses having absorption bands that at least partially fall within other wavelength bands may also be detected.

The scope of the invention is defined by the claims, which are incorporated into this section by reference. A more complete understanding of embodiments will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments and their advantages are best understood by referring to the detailed description that follows. It should be appreciated that like reference numerals are used to identify like elements illustrated in one or more of the figures.

DETAILED DESCRIPTION

Definitions

The term irradiance as used herein is defined as the total power including all wavelengths of electromagnetic radiation at a surface per unit surface area, and is generally measured in $W/m^2$ or equivalent units.

The term spectral irradiance as used herein is defined as the power per unit area per unit wavelength of electromagnetic radiation at a surface, and is generally measured in $W/m^2/nm$.

The term transmittance as used herein is defined as a ratio expressed as a percentage of radiation intensity transmitted through a medium (I) to radiation intensity incident on the medium ($I_0$), at a specified wavelength. In one embodiment, an optical band pass filter may have a transmittance of 99.9% at a wavelength of 10 µm and a transmittance of less than 2% at wavelengths less than 9 µm and greater than 11 µm. Other optical band pass filters with other transmittance percentages and/or other wavelengths are also contemplated.

The term photo current as used herein is defined as a current generated by a photo sensor in response to irradiance at an active surface of the photo sensor and may be measured in mA.

The term spectral responsivity as used herein is defined as the ratio of photo current generated by a photo sensor per unit irradiance at an active surface of the photo sensor per unit wavelength and may be measured in mA/W/nm or other suitable units.

The term Group III-V semiconductor compounds refers to semiconductor compounds of group III and/or group V elements of the periodic table of elements and includes aluminum phosphide, aluminum arsenide and gallium arsenide.

The acronym QWIP as used herein stands for a quantum well infrared photo detector (e.g., sensor).

Referring to FIG. 1 a camera system 100 (e.g., an infrared camera system having a plurality of QWIPs tuned to detect a limited spectral bandwidth of infrared radiation corresponding to at least a portion of an infrared absorption band of one or more gasses), in accordance with an embodiment, comprises a housing 102 and a lens 104 (e.g., a lens element) extending out from the housing 102. The lens 104 and housing 102 may be configured with lens mounting hardware for removing the lens and attaching other interchangeable lenses as may be required. The lens 104 is configured as an infrared wavelength imaging lens for collecting infrared radiation from a scene 106 over a field of view. The field of view is defined by an angle α (also referred to as a field of view angle, a solid cone angle, and a horizontal scene angle), which may be defined by a round aperture inside the lens 104. The lens 104 is configured to form a focused image of the scene 106 onto an active area of a focal plane array (FPA) 108, which is positioned coincident with a focal plane of the lens 104. The lens 104 and FPA 108 may be configured such that the lens 104 forms a focused image of the scene that completely fills the FPA active area.

Generally, angle α corresponds with a particular image magnification with larger angles corresponding with lower image magnification values than smaller angles. The camera system 100 is configured to accept a plurality of interchangeable lenses 104 usable for different situations with each lens being configured to position its focal plane coincident with the active area of the focal plane array 108. In one embodiment, the camera system 100 may be configured to operate with three different interchangeable lenses 104 with each lens having a different focal length, magnification, and angle α. In one example, a first lens has a focal length of 25 mm and projects an angle α of 22° onto the FPA 108, a second lens has a focal length of 50 mm and projects an angle α of 11° onto the FPA 108 and a third lens has a focal length of 100 mm and projects an angle α of 5.5° onto the FPA 108. Preferably each lens 104 is formed from suitable optical materials and aberration corrected over a wavelength range (e.g., a wavelength range that at least includes 10.4-10.8 µm or another wavelength range) in order to form a substantially diffraction limited infrared image of the scene 106 onto the FPA active area. Additionally, the lens elements may be coated to reduce reflectivity at a wavelength range (e.g., a wavelength range that includes 10.4-10.8 µm or another wavelength range). Each lens 104 may be constructed with baffles, apertures and the like, and with the optical elements treated with surface coatings to prevent stray radiation from reaching the FPA active area. Each lens 104 also may be equipped with an operator adjustable or an automatically adjusted focusing mechanism constructed to adjust the sharpness of the scene image formed on the FPA active area. In addition, the camera system 100 and/or lens 104 may include one or more operator adjustable or automatically adjustable mechanical, electrical or electro-optical devices configured to ensure that radiation reaching the FPA 108 is within irradiance limits suitable for rendering an acceptable digital image of the scene 106. In addition, the camera system 100 may be equipped with a digital zoom system for adjusting image magnification and field of view using digital image zooming techniques.

An optical band pass filter 110 is positioned between the lens 104 and the FPA 108 and functions to limit the spectral band width of radiation reaching the active area of the FPA 108. In one embodiment, the band pass filter 110 comprises an optical substrate having two opposing and substantially parallel optical surfaces separated by a substrate thickness and formed with a clear aperture usable for spectrally filtering light entering the lens 104 over angle α. The band pass filter 110 is positioned with its opposing surfaces oriented substantially parallel to the active area of the FPA 108. The optical substrate may comprise optical quality germanium or another suitable substrate with one or both of the opposing surfaces being coated with one or more thin film layers configured to provide a filter spectral transmittance profile that limits the spectral band width of radiation that passes through the band pass filter 110. Alternately, the band pass filter 110 may comprise a plurality of optical substrates bonded or otherwise sandwiched together with more than two opposing optical surfaces and more than two surfaces coated with thin film layers.

Typically, the band pass filter 110 has a substantially Gaussian shaped spectral transmittance profile having a peak or near peak transmittance over a first wavelength band, a full width half maximum spectral transmittance separated by a second wavelength range and spectral transmittance profile edges separated by a third wavelength range. In one embodiment, the spectral transmittance profile has a transmittance of less than about 0.1% for wavelengths not included within the third wavelength range defined by the spectral transmittance profile edges.

In one example, the band pass filter 110 has a spectral transmittance profile that includes a peak or near peak transmittance of 85% substantially at 10.57 µm such that the band pass filter is tuned to an absorption band of the compound $SF_6$. Additionally, in a first embodiment of the band pass filter 110 the spectral transmittance profile has a full width half maximum transmittance bandwidth of approximately 10.4-10.8 µm and spectral transmittance profile edges occurring at 10.38 and 10.82 µm respectively. Another embodiment of the band pass filter spectral transmittance profile is defined in TABLE 1 which is slightly shifted to ensure that the band pass filter 110 includes portions of the absorption band of $SF_6$ approximately centered at 10.57 µm as well as an absorption band of the compound ammonia, ($NH_3$) which has a strong infrared absorption band approximately centered at 10.36 µm. In this example, the band pass filter 110 has a full width half maximum transmittance bandwidth that overlaps an absorption band of $SF_6$ and $NH_3$. Other band pass filter 110 implementations with other spectral transmittance profiles are also contemplated.

TABLE 1

BAND PASS FILTER TRANSMITTANCE

| | |
|---|---|
| Peak Transmittance (at 10.57 µm) | Greater than or equal to 85% |
| Transmittance at 10.30 µm to 10.70 µm | 50% of peak transmittance |
| Transmittance from UV-10.28 µm | 0.1% |
| Transmittance from 10.72 µm-14.0 µm | 0.1% |
| Slope | Less than 2% |

Figure 2:
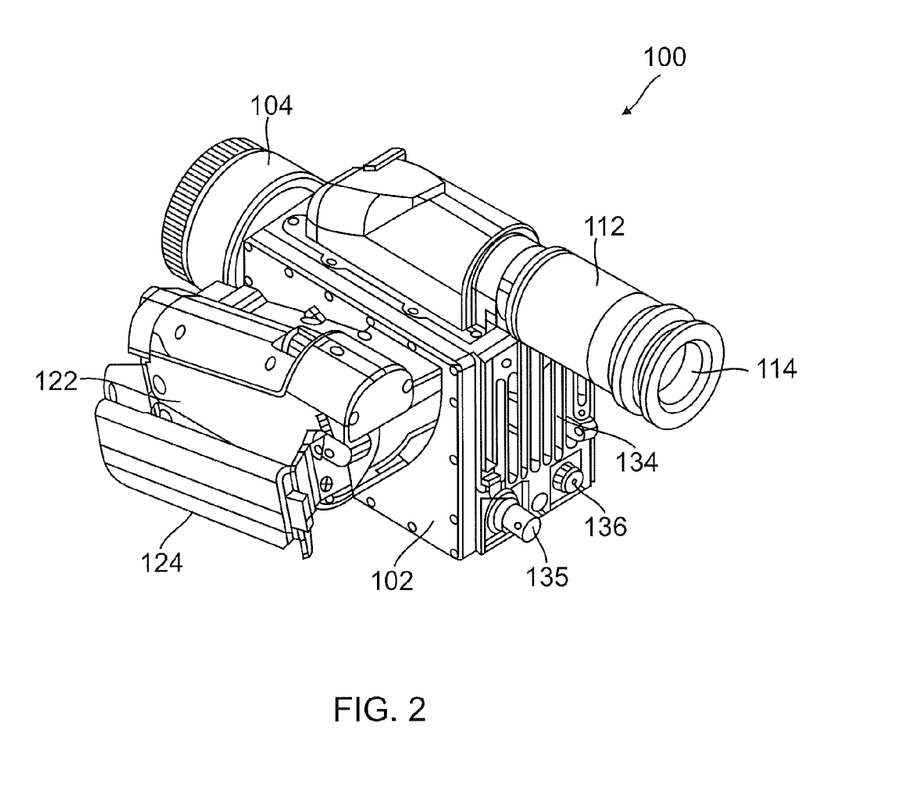
FIG. 2 illustrates an isometric view of a camera system in accordance with an embodiment.

Referring now to FIGS. 1 and 2, FIG. 2 depicts an isometric external view of an embodiment of a camera system 100. The lens 104 is shown extending out from a front end of the housing 102 and a view finder assembly 112 extends upward from the housing 102 at a top side thereof. The view finder assembly 112 is pivotally supported with respect to the camera housing top side to allow a user to pivot the view finder assembly 112 to a range of viewing positions as may be required. The view finder assembly 112 includes an eyepiece opening and eyepiece 114 provided to allow a user to view a display device 116 (e.g., a video display or other appropriate display device), housed inside the camera system 100, through the eyepiece 114. In one embodiment, the display device 116 displays a live black and white video image of the scene 106 as formed by the FPA 108 and as processed by an optical signal processor, (OSP) 118. Alternately the display device 116 may display a live color video image of the scene 106. Accordingly, a user looking into the view finder assembly 112 views the live video image of the scene 106 and adjusts the camera pointing direction, lens focus, digital zoom, and other user controls to view and analyze elements of the scene image as required. Moreover, since the camera system 100 may be used outdoors, the display device 116 and eyepiece 114 viewing are provided to improve image contrast even in direct sunlight to improve the leak plume detection.

The camera system 100 includes a central processing unit (CPU) 126 interconnected with a digital data storage module 130, a user interface module (UIM) 128, a power module 120, a cooling module 190 (e.g., a refrigeration device), an optical signal processing module (OSP) 118, a video driver module 132, and an associated display device 116. The CPU 126 interfaces with the digital data storage module 130 to exchange digital data therewith for receiving operating program steps stored in the digital data storage module 130 and executing the operating programs steps in accordance with preset operating modes and conditions and further in accordance with user input commands received from a user through the UIM 128.

Generally, the camera system 100 operates to form an image of the scene 106 onto the FPA 108, render a digital image of the scene 106 in a video image frame format, display the video image frame on the display device 116, or deliver the video image frame out of the camera system 100. Alternately, video image frames may be stored on the digital data storage module 130. In addition, the camera system 100 is configured to update video image frames at one or more video frames rates ranging from 15-100 cycles per second.

The CPU 126 may comprise a commercially available integrated circuit microprocessor chip and the microprocessor chip may include digital data processing hardware, memory registers and cache memory for temporary data storage.

The digital data storage module 130 may comprise one or more permanently installed or removable memory devices using solid state, optical or magnetic memory storage devices including solid state random or dynamic access memory (RAM, DRAM), non-volatile FLASH memory, optical compact disk memory, (CD) digital video disk memory (DVD), magnetic hard or soft disk memory, and the like.

The UIM 128 comprises a plurality of user interface control elements such as one or more toggle switches, variable position dials, knobs, key pads, or the like, positioned on external surfaces of the housing 102 and ideally positioned for ergonomic operation of the camera system 100 while looking through the eyepiece 114. The user interface control elements allow a user to select various camera operating modes, power modes, lens modes, video display modes, and the like, as may be required. Each user selection includes the actuation of a user input device and a signal generated by the actuation and communicated to the CPU 126 to reconfigure camera operation according to user input commands. In addition, the UIM 128 may interface with a video driver module 132 to display text and graphics on the display device 116 such as for displaying menus, status indicators, warnings, or the like in a text and graphic form that is easily interpreted by a user viewing the display device 116 through the eyepiece 114.

The text and graphics may be displayed on the display device 116 simultaneously with a live or still video image of the scene 106 received from the OSP 118 such that camera operating conditions and the like may be displayed at edges of the display screen during live imaging by the camera system 100. Alternately, the entire display device 116 may be filled with a menu, or the like, to allow the user to set or review various camera parameters, conditions, or settings. Accordingly, a user may operate the camera system 100 to view a live scene image while simultaneously viewing camera status and mode conditions through the eyepiece 114 and the user may use fingers and thumbs to actuate switches/actuators/keypads and the like disposed on outside surfaces of the housing 102 to adjust or reset camera operating conditions while viewing a live image.

The camera system 100 includes power module 120 and an input output (I/O) module 134. The power module 120 comprises a battery and other power distributing and conditioning elements. The battery is housed in a battery compartment generally indicated by reference numeral 122. The battery compartment 122 also serves as a user handle and includes a flexible strap 124 attached thereto to provide improved user gripping. The front side of the battery compartment may include a hinged door, not shown, through which the rechargeable battery may be installed and removed. The battery may comprise a commercially available high capacity rechargeable nickel metal hydride (NIMH), nickel cadmium (NiCd), or lithium ion (LiION), battery and the camera system 100 may be sold with a separate battery charger. Alternately, any other self contained power source may be used to provide a source of power to the camera system 100.

Additionally, the power module includes one or more input terminals, associated with the I/O module 134, for receiving power inputs from a DC power source, such as a vehicle power system, or from an AC power source such as a conventional building power system. The power inputs may be used to operate the camera directly, to recharge a battery installed in the battery compartment 122, or both. The power module 120 may also include control systems such as sensors, switches, power conditioning elements, and the like, all interfacing with the CPU 126 and operable according to power module program operating steps stored in the digital data storage module 130. Generally, the power module 120 interfaces with and distributes power to camera systems that require power and may shut off automatically or reduce power consumption when appropriate.

The I/O module 134 includes various wire connecting ports extending through the housing 102 and interfacing with internal systems and may include a wireless transceiver for communicating with external devices over radio or microwave frequencies. In particular, the I/O module 134 includes power input ports, a digital video output port 135 (e.g., an I/O module connector) for interfacing with an external video display device and an analog video output port 136 for interfacing with a video storage and/or display device configured to receive separate video, (S-video). In particular, the camera system 100 may be sold with a separate video recording device usable to store and display video images for remote viewing.

Figure 3:
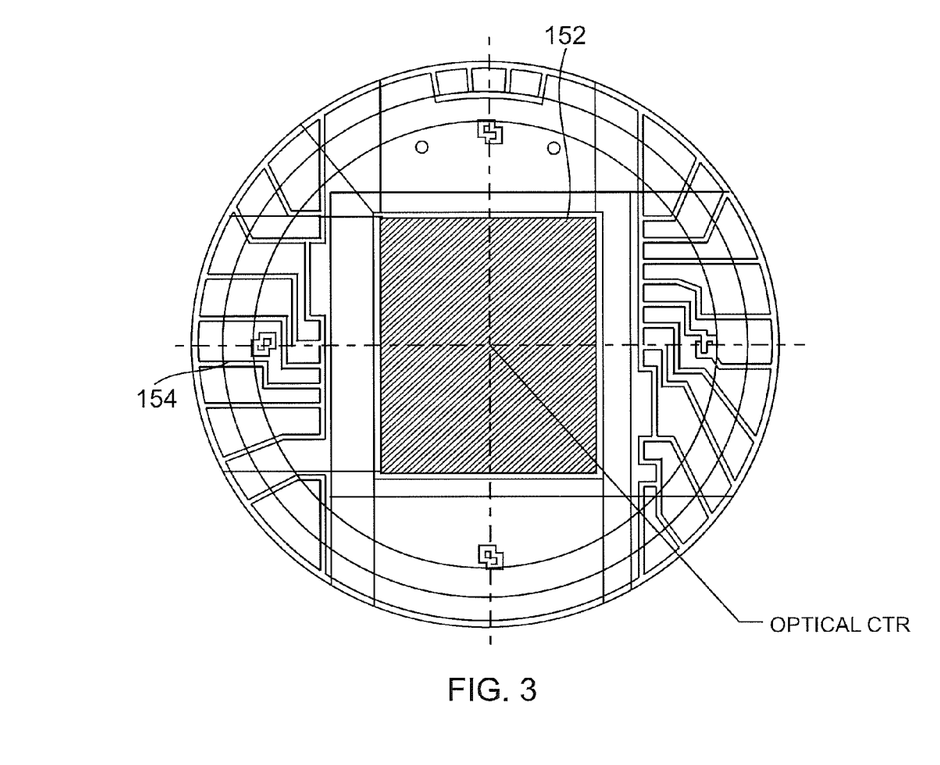
FIG. 3 illustrates a top view of a focal plane array supported on a support substrate in accordance with an embodiment.
Figure 4:
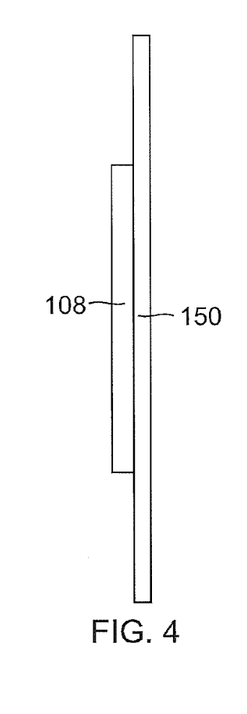
FIG. 4 illustrates a side view of a focal plane array supported on a support substrate in accordance with an embodiment.

Referring to FIGS. 3 and 4, the FPA 108 is shown mounted on a support substrate 150. The FPA 108 includes an active area 152 comprising a two dimensional array of photo sensor elements. The active area is positioned in a focal plane of the lens 104 and receives radiation from the scene 106 through the lens 104 and band pass filter 110.

Each photo sensor is constructed to generate a photo current or other electrical photo signal in response to radiation falling thereon. The amplitude of the photo current is proportional to the irradiance and wavelength of radiation incident on the sensor surface. Ideally, each sensor in the array has a substantially uniform responsivity profile, e.g. photo current amplitude, generated in response to a given irradiance at a given wavelength. However in practice, the responsivity profile of individual sensor elements varies from element to element and must be corrected using a calibration function. Each photo sensor may generate a substantially linear photo current output over a limited range of input irradiance and a non-linear photo current output outside the linear range. Accordingly, the camera system 100 may include devices constructed to maintain sensor irradiance within the range that produces a linear photo current output, and/or the camera system 100 may include electronic or digital systems configured to render a corrected image when irradiance levels at the sensor surfaces are outside the desired operating range.

Sensor elements of the active area 152 are arranged in a two dimensional array of rows and columns. In one example, the active area 152 comprises and array of 320×256 sensing elements with approximate array dimensions 9.6×7.7 mm and with each sensor element centered within a unit cell having approximate dimensions of 30 µm×30 µm. The FPA 108 further includes a conventional silicon complementary metal-oxide-semiconductor (CMOS) readout integrated circuit 154 positioned between the active area 152 and support substrate 150 and interconnected to each individual sensor element through an indium bump, or other suitable connector, extending between each sensor element and the readout circuit 154.

The FPA 108 and readout circuit 154 are bonded or otherwise attached to the support substrate 150. The support substrate 150 comprises an electrically insulating material, such as a sapphire or alumina substrate. In one example, the support substrate 150 is circular having an outside diameter of approximately 21.1 mm, (0.83 inches) and a thickness of approximately 0.5 mm, (0.197 inches) and supports the active area 152 substantially centered on the support substrate 150. The readout circuit 154 is configured to integrate individual sensor photo current responses over time and to periodically deliver an integrated signal value out from the readout circuit 154 to the optical signal processor (OSP) 118. The readout circuit 154 also applies a bias voltage to sensor elements and may include an electrical gain circuit and other circuit elements for amplifying and otherwise modifying sensor photo response signals as may be required. In addition, parameters of the readout circuit 154, particularly integration time, may be controlled by the CPU 126 and modified according to image conditions, user input commands, or both.

The signals are delivered out from the readout circuit 154 over wire bonded connections extending between terminal points on the readout circuit 154 and electrical output terminals 156. Each output terminal 156 (FIG. 5) may be associated with a plurality of individual photo sensor elements, e.g. an entire row or column of sensor elements. The output terminals 156 extend from inside a dewar assembly, shown in FIG. 5 and described below, to a connector interface suitable for connection with the OSP 118.

The OSP 118 includes circuits configured to digitize individual sensor element photo signals by converting each analog signal received from each photo sensor to a digital equivalent black and white grey scale gradation value, or the like. Each gradation value is a whole number ranging from a minimum value for white corresponding with a selected minimum photo sensor response signal and a maximum value for black corresponding with a selected maximum photo sensor response signal and with intermediate values corresponding with intermediate grey scale levels according to a substantially linear scale. Typical digital grey scale values range from 1 to 256 or 1 to 64K, however other ranges are usable. For each video frame, the OSP 118 assigns each sensor element with a grey scale pixel value corresponding with the irradiance generated by the scene 106 at the sensor element and assembles the video frame for storage in a frame buffer or delivery out from the OSP. The video image may be rendered with one pixel corresponding to each sensor element or with more than one sensor element being associated with each pixel.

The OSP 118 is configured to apply biases and/or corrections to individual pixel values to: (a) correct for differences in sensor element to sensor element responsivity profiles; (b) adjust the dynamic range of the image; (c) account for non-scene noise generated by a bias voltage applied to the sensor elements; (d) change the video frame rate; (e) filter out noise or static non-scene image artifacts; and/or (f) make other adjustments as may be required to enhance the video image and to extract as much scene information from the image as may be used. Additionally, the OSP 118 is configured to contour the video image by rendering a video image with a compressed grey scale range for displaying scene energy contours. Alternately, the OSP 118 is configured to assign colors to grey scale gradation values or groups of grey scale values to render a color image of the scene 106 with different colors corresponding to different sensor irradiance values. Moreover, the OSP 118 is configured to reverse gray scale values for generating reverse images and may apply other adjustments to the linearity of gray scale value assignment to extract as much scene information from the image as may be used Once each scene video image is assembled and corrected by the OSP 118, the scene video image is delivered to the video driver module 132 or may be delivered out from the camera system 100 through the I/O module 134. The video driver module 132 formats the scene video image for display on the camera internal display device 116 or for display on an external display device connected to the digital video output port 135. The video driver module 132 is configured to add text and graphics to each video image to display information on the display device 116 simultaneously with the display of a video image of the scene 106. The displayed information may comprise a camera operating mode, high or low irradiance warnings, focus conditions, lens type, imaging mode parameters and other conditions as may be useful. Additionally, the video driver module 132 may be configured to display a cursor or other movable display element over the video image being displayed. In one embodiment, a cursor may be locked to an image feature, e.g. the brightest pixel in the image, and the cursor may follow the position of the brightest pixel in the image as each video frame is updated. Additionally, the video driver module 132 may be configured to display a menu on the display device 116 and to receive commands from a user interface keypad, or the like, for displaying user entries or for moving a cursor over the displayed menu in response to a users commands. Additionally, the video driver module 132 may be configured to display individual video image frames, to display a plurality of video image frames in a thumb nail display mode, and/or to display a still or video images in other modes as may be required. Additionally, the video driver module 132 may be configured to display date, time, camera global position coordinates, scene names and/or any other information that may be useful. Additionally, the camera system 100 may be configured to store one or more video image frames, including any text or graphic information displayed simultaneously with the video image on the digital data storage module 130, or to deliver video image frames out of the camera through the I/O module 134.

Figure 5:
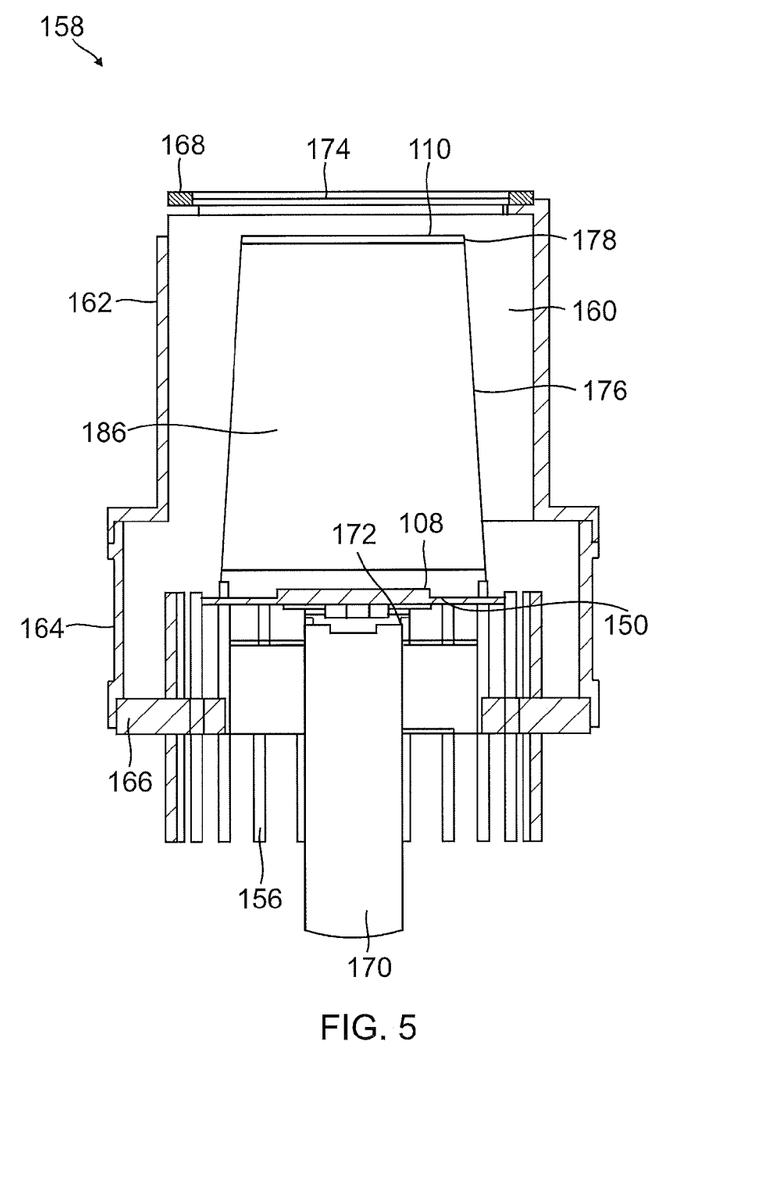
FIG. 5 illustrates a section view taken through a dewar assembly in accordance with an embodiment.

Referring now to FIG. 5, a section view shows the support substrate 150 and FPA 108 supported inside a dewar assembly, generally indicated by reference numeral 158. The dewar assembly 158 generally encloses a substantially cylindrical hollow vacuum cavity 160 formed by annular sidewalls 162 and 164, a base wall 166 and a top wall 168, all laser welded or otherwise suitably joined together to provided the vacuum tight enclosure 160 which is drawn to a low vacuum pressure, e.g. $10^{-8}$-$10^{-10}$ Torr. The base wall 166 includes a sealed aperture passing there through for receiving a cold finger 170 into the vacuum cavity 160 and the cold finger is formed with a thermally conductive end cap 172 configured to attach to and support the support substrate 150. The dewar assembly top wall 168 includes an aperture passing there through for receiving an IR transparent window 174 therein and supported by the top wall 168. The transparent window 174 admits IR radiation received from the lens 104 into the hollow vacuum cavity 160.

A stray light baffle 180 comprises an annular sidewall 176 extending between the support substrate 150 and a light baffle top wall 178. The light baffle top wall 178 includes an aperture passing there through and the band pass filter 110 is supported within the aperture by the light baffle top wall 178. The stray light baffle 180 is formed from a thermally conductive material with the annular side wall 176 formed cone-shaped such that the annular side wall 176 and a clear aperture of the band pass filter 110 work together to limit radiation falling onto the FPA active area 152 to only radiation received from the field of view of the lens 104. Additionally, surfaces of the stray light baffle 180 are shaped and treated to absorb or otherwise prevent stray radiation, e.g. reflected or emitted from other local surfaces from reaching the active area 152.

The cold finger 170 extends from the cooling module 190 of FIG. 1 (e.g., a high performance Stirling cycle refrigeration device housed within the housing 102). In one embodiment, the cooling module 190 operates to cool the end cap 172 to a temperature of approximately 65K or less and preferably 55° K. The end cap 172 is positioned in contact with the support substrate 150, which provides an efficient thermally conductive pathway extending from the end cap 172 to the FPA 108 and to the light baffle annular wall 176. Additionally, the light baffle annular wall 176 provides an efficient thermally conductive pathway to the band pass filter 110. After an initial cool down period, e.g. 1-10 minutes depending upon the thermal load, the cooling module 190 draws enough thermal energy away from the FPA 108, stray light baffle 180 and band pass filter 110 to substantially cool each element to an operating temperature of approximately 55° K. This prevents the cooled element from emitting a radiation signal that may be detectable by the active area 152, and in the case of the FPA 108 from generating a thermally induced electrical signal (dark current) that may contribute unwanted electrical noise to the scene image. Thus, according to one or more embodiments, the FPA 108, stray light baffle 180, and band pass filter 110 are cooled to an operating temperature of approximately 55° K. Moreover, the evacuated vacuum cavity 160 acts as a thermal insulator to thermally isolate the cooled elements from the ambient surroundings.

In another aspect according to one or more embodiments, each individual sensor of the FPA 108 comprises a quantum well infrared photo detector, (QWIP). In one embodiment, each QWIP has a peak spectral responsivity approximately in the range of 10.4-10.8 µm and a full width half maximum spectral bandwidth of less than 1.0 µm and preferably less than about 0.7 µm. In this embodiment, each QWIP is constructed with a spectral responsivity at 10.6 µm that is at least 80% of the peak spectral responsivity. In other embodiments, the QWIPs may be implemented with other spectral responsivity and spectral bandwidth characteristics.

Generally the QWIP is constructed from III-V compound semiconductors such as gallium arsenide, (GaAs), and aluminum gallium arsenide (AlGaAs) formed in thin alternating layers of GaAs quantum wells, and AlGaAs barriers. The well layers are doped with electron donor impurities, e.g. silicon, or other suitable doping materials, to generate a desired flow of free electrons in the well layers. Generally, the peak response wavelength and the spectral band width of the photo response of a QWIP is determined by the thicknesses and compositions of the well and barrier layers. In one embodiment, the thickness and composition of the QWIP layers are selected to absorb photons with wavelengths in the range of 10.4 to 10.8 µm to generate a peak photo current in response to absorbing such photons. In this embodiment, with responsivity tuned to the wavelength range of 10.4 to 10.8 µm, the susceptibility of the QWIP to generate an undesirable dark current is increased as compared to detectors having responsivity at smaller wavelengths such as the 3.0-5.0 µm range used for methane imaging. In other embodiments, the thickness and composition of the QWIP layers may be selected to absorb photons with wavelengths in other ranges.

Generally, dark current is the current generated by a photo sensor in response to a substantially negligible irradiance received from a survey scene, (e.g. with the lens cap blocking the camera lens), such that dark current is signal noise. Dark current is generated in response to IR radiation that is emitted by the FPA 108, the support substrate 150, the stray light baffle 180 and the band pass filter 110. The spectral bandwidth of the IR radiation emitted by local elements depends on the absolute temperature of the local elements. In one embodiment, the local elements are maintained at an absolute temperature of less than 65° K to reduce the amount of IR radiation that the local elements emit in the wavelength range of 10.4 to 10.8 µm. Ideally, the local elements are maintained at an absolute temperature of less than 55° K. In other embodiments, the local elements may be maintained at other appropriate absolute temperatures to reduce the amount of IR radiation that the local elements emit in other wavelength ranges.

Generally, the camera system 100 operates to render a video image of a scene. While radiation energy received from the scene may have a wide spectral bandwidth, in one embodiment, the FPA 108 is constructed with QWIPs that generate a peak photo current response in the wavelength range of 10.4 to 10.8 μm and have a full width half maximum spectral bandwidth of less than 2.0 μm and preferably with a spectral bandwidth of 0.7-1.0 μm. This reduces signal noise generated by the background of the scene and by elements of the camera itself to increase contrast between a leak plume and the scene background. Also, in this embodiment, the camera system 100 may include a narrow band pass filter 110 having a peak transmittance within the wavelength range of 10.30 to 10.70 μm and having considerably less transmittance (e.g., 0.1% of the peak transmittance outside the wavelength range of 10.28 μm to 10.72 μm). Also, in this embodiment, other optical filter spectral transmittance profiles that include the spectral range 10.4-10.8 μm are also usable. Also, in this embodiment, the focal plane array 108, band pass filter 110 and other local support elements are enclosed in a vacuum cavity to thermally isolate them from the camera body and surrounding air and cooled to 65° K or less by the cooling module 190 (e.g., a refrigeration device housed with the camera system 100) to further reduce dark current in the FPA 108 and to reduce thermal radiation from elements surrounding the FPA 108.

Referring again to the embodiment of camera system 100 described above, generally all areas of a scene include some level of radiation in the spectral bandwidth 10.3-10.8 μm. However, areas of the scene that are absorbing radiation in the spectral bandwidth 10.3-10.8 μm will have less radiation in that spectral bandwidth range than other areas of the scene. Accordingly, when the scene is imaged onto the FPA 108 and filtered by the band pass filter 110, areas of the scene having low radiation levels will generate low irradiance levels at corresponding sensor surfaces and will generate low photo currents in the FPA 108. Thus, areas of the scene that are absorbing radiation that falls within the narrow bandwidth of the scene image (10.3-10.7 μm or 10.4-10.8 μm depending on the optical filter used) will be readily distinguishable from other areas of the scene when the scene image is rendered as a video image and viewed by a user. Compounds (gasses, liquids or solids) having an infrared absorption band that at least partially overlaps the spectral band 10.3 to 10.7 μm, (or 10.4 to 10.8 depending on the filter used) may be viewed in the scene image.

One example compound that may be imaged using the embodiment of camera system 100 described above is sulfur hexafluoride ($SF_6$) which has a strong infrared absorption band that extends from about 10.51-10.65 μm with a peak absorption approximately centered at 10.57 μm. $SF_6$ is a gas used as an electrical insulator in power distribution equipment and the like, as a cover gas over molten magnesium to minimize oxidation, and as an agent for improving process performance in semiconductor manufacture. Additionally, $SF_6$ is a potent greenhouse gas that may contribute to environmental damage when it is released e.g. by leaks.

Another example compound that may be imaged using the embodiment of camera system 100 described above is ammonia, ($NH_3$) which has a strong infrared absorption band approximately centered at 10.36 μm. $NH_3$ is used as a reagent to produce nitric acid, as a fertilizer, as a refrigerant, as a disinfectant, a solvent, and has many other uses. However, ammonia is toxic to mammals and may be harmful when released, e.g. by leaks.

Another example compound that may be imaged using the embodiment of camera system 100 described above is uranyl fluoride ($UO_2F_2$). $UO_2F_2$ is created when uranium hexafluoride ($UF_6$) leaks into the atmosphere. $UF_6$ is a gaseous compound used in uranium enrichment and is the compound to which most depleted (waste) uranium is converted for long term storage in gas cylinders. It is desirable to detect and repair leaks in $UF_6$ containers and to look for $UF_6$ to detect uranium enrichment activity by detecting the local presence of uranyl fluoride ($UO_2F_2$).

Advantageously, the QWIPs of FPA 108 may be tuned to detect various limited spectral bandwidths of infrared radiation. These limited spectral bandwidths may correspond to, for example, at least a portion of an infrared absorption band of one or more substances such as gasses present in scene 106 (for example, infrared radiation in portions of the longwave infrared spectrum). Band pass filter 110 may be configured to substantially filter out infrared radiation outside of the limited spectral bandwidth to which QWIPs are tuned. As a result, camera system 100 may be particularly well calibrated to detect many different types of substances present in scene 106. In one embodiment, the QWIPs of FPA 108 and the band pass filter 110 may be tuned (e.g., calibrated) based on spectral bandwidths of infrared radiation (e.g., infrared spectra) associated with various substances as identified by the National Institute of Standards and Technology (NIST) and available through the Internet at http://webbook.nist.gov/chemistry/. The following TABLE 2 identifies several examples of substances which may be detected by appropriate tuning of FPA 108 and band pass filter 110.

TABLE 2 acetic acid
acetyl chloride
allyl bromide
allyl chloride
allyl fluoride
ammonia
anhydrous ammonia
bromomethane
chlorine dioxide
cyclosarin (GF)
cyclotrimethylenetrinitramine (RDX)
ethyl cyanoacrylate
ethylene
freon ® 11
freon ® 12
furan
HD (Bis-(2-chloroethyl) sulfide)
hydrazine
hydrogen sulfide
methane
methyl ethyl ketone
methyl vinyl ketone
methylsilane
nitrobenzene
picric acid
propenal
propene
sarin (GB)
soman (GD)
sulfur dioxide
sulfur hexafluoride (SF6)
tabun (GA)
tetrahydrofuran
trichloroethylene
trinitrotoluene (TNT)
uranyl fluoride
vinyl chloride
vinyl cyanide
vinyl ether
VX (S-[2-(diisopropylamino)ethyl]-O-ethyl methylphosphonothioate)

In one embodiment, camera system 100 may be used to provide an image of one or more gasses, such as gasses identified in TABLE 2, or other gasses identified herein. In this embodiment, lens 104 receives infrared radiation from survey scene 106 which includes one or more gasses. Band pass filter 110 filters the infrared radiation to a wavelength range including a limited spectral bandwidth of the infrared radiation. This limited spectral bandwidth corresponds to at least a portion of an infrared absorption band of one or more of the gasses. FPA 108 receives the filtered infrared radiation and includes a plurality of QWIPs tuned to detect the limited spectral bandwidth of the infrared radiation. FPA 108 provides a plurality of signals to OSP 118 in response to the filtered infrared radiation. OSP renders an image of one or more of the gasses in response to the signals. For example, the image may be provided to digital video output port 135 or analog video output port 136 to pass the image to an external device. In another example, display device 116 may provide the image to a user for viewing (e.g., through eyepiece 114).

In another embodiment, camera system 100 may be operated by a user to detect one or more gasses, such as gasses identified in TABLE 2, or other gasses identified herein. In this embodiment, a user positions camera system 100 to receive infrared radiation from survey scene 106 which includes one or more gasses. For example, a user may orient lens 104 in the direction of scene 106. Also in this embodiment, camera system 100 renders and displays an image of one or more gasses, for example, on display device 116. The user then views the image, for example, through eyepiece 114. Through inspection of the displayed image, the user may determine the presence or absence of one or gasses in scene 106.

In another embodiment, camera system 100 may be manufactured by selecting lens 104, forming QWIPs of FPA 108, and selecting band pass filter 110. In this embodiment, an appropriate implementation of lens 104 may be selected which is adapted to receive infrared radiation from scene 106 comprising one or more gasses. Also in this embodiment, the QWIPs may be formed such that they are tuned to detect a limited spectral bandwidth of the infrared radiation corresponding to at least a portion of an infrared absorption band of the one or more gasses. Further in this embodiment, an appropriate implementation of band pass filter 110 may be selected which is adapted to filter the infrared radiation to a wavelength range substantially corresponding to the limited spectral bandwidth of the QWIPs.

In another embodiment, an image of a scene 106 is collected by the lens 104, spectrally band pass filtered by the band pass filter 110, focused onto the FPA 108 by the lens 104, rendered as a video image by the OSP 118, configured for display by the video driver module 132 and displayed by the display device 116. More specifically, the image focused onto the FPA 108 has a spectral bandwidth in the range of 10.3-10.7, 10.4-10.8 µm, or other range depending on the spectral transmittance of the band pass filter 110. The video image is rendered by assigning the lowest grey scale values to the lowest levels of photo current generated by the FPA 108 in response to the image focused onto the FPA 108, by assigning the highest grey scale values to the highest levels of photo current generated by the FPA 108 in response to the image focused onto the FPA 108, and by assigning intermediate grey scale values to intermediate levels of photo current generated by the FPA 108 in response to the image focused onto the FPA 108. These assignments are accomplished in a substantially linear distribution of grey scale values.

In another embodiment, the camera system 100 may be operated to reverse the grey scale polarity of video images of the scene by assigning the highest grey scale values to the lowest levels of photocurrent.

In another embodiment, the camera system 100 may be operated to render color video images of the scene by assigning a different color to different levels of photocurrent.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications, e.g. imaging gas leak plumes for compounds having absorption bands approximately in the spectral bandwidth of 10.3-10.8 µm or other spectral bandwidths, those skilled in the art will recognize that its usefulness is not limited thereto and that one or more embodiments may be beneficially utilized in any number of environments and implementations including but not limited to any other application wherein it would be useful to generate a video image of a compound having an absorption band that may be detected by a QWIP or other narrow spectral bandwidth detector tuned to the absorption band of the compound.

Embodiments described above illustrate but do not limit the invention. It should also be understood that numerous modifications and variations are possible in accordance with the principles described herein. Accordingly, the scope of the invention is defined only by the following claims.

What is claimed is:

1. An infrared camera system, comprising:
   a lens adapted to receive infrared radiation from a survey scene comprising one or more gasses;
   a focal plane array comprising a plurality of quantum well infrared photo detectors (QWIPs) comprising:
      a plurality of quantum well layers comprising gallium arsenide (GaAs) doped with silicon to generate a desired flow of free electrons in response to the radiation,
      a plurality of barrier layers alternating with the quantum well layers and comprising aluminum gallium arsenide (AlGaAs), wherein:
         the quantum well layers and the barrier layers have associated thicknesses,
         an amount of silicon doping, a spacing of quantum wells in the quantum well layers, and the thicknesses of the quantum well layers and the barrier layers are selected for the QWIPs to tune the QWIPs to have a limited spectral bandwidth with a peak response within a wavelength range of 10.4 µm to 10.8 µm corresponding to at least a portion of an infrared absorption band of the one or more gasses and to have a full width half maximum spectral bandwidth of less than 0.7 µm in response to the radiation; and
   an optical band pass filter positioned substantially between the lens and the focal plane array and adapted to filter the infrared radiation to a wavelength range substantially corresponding to the limited spectral bandwidth of the QWIPs before the infrared radiation is received by the focal plane array, wherein the less than 0.7 µm spectral bandwidth of the focal plane array is selected to reduce signal noise substantially outside the wavelength range of 10.4 µm to 10.8 µm associated with the optical band pass filter and/or the focal plane array.

2. The infrared camera system of claim 1, wherein:
   the focal plane array is adapted to provide a plurality of signals in response to the filtered infrared radiation;

the less than 0.7 μm spectral bandwidth of the focal plane array is selected to reduce dark current associated with the optical band pass filter and/or the focal plane array; and the system comprising a processor adapted to render an image of the one or more gasses in response to the signals.

3. A method of providing the image of the one or more gasses using the infrared camera system of claim 2, the method comprising:

receiving the infrared radiation through the lens;
filtering the infrared radiation to the wavelength range comprising the limited spectral bandwidth using the optical band pass filter;
receiving the filtered infrared radiation at the focal plane array;
providing the signals from the focal plane array to the processor; and
rendering the image using the processor.

4. The infrared camera system of claim 2, comprising an output port adapted to pass the image to an external device.

5. The infrared camera system of claim 2, comprising a display adapted to provide the image to a user for viewing.

6. The infrared camera system of claim 1, wherein the lens is adapted to focus the infrared radiation at a focal plane substantially coincident with the focal plane array.

7. The infrared camera system of claim 1, wherein the limited spectral bandwidth of the infrared radiation is longwave infrared radiation.

8. The infrared camera system of claim 1, wherein the one or more gasses include a gas leak plume.

9. The infrared camera system of claim 1, wherein the one or more gasses include a gas identified in TABLE 2.

10. A method of manufacturing an infrared camera system, the method comprising:

selecting a lens adapted to receive infrared radiation from a survey scene comprising one or more gasses;
forming a focal plane array comprising a plurality of quantum well infrared photo detectors (QWIPs) comprising:
a plurality of quantum well layers comprising gallium arsenide (GaAs) doped with silicon to generate a desired flow of free electrons in response to the radiation,
a plurality of barrier layers alternating with the quantum well layers and comprising aluminum gallium arsenide (AlGaAs), wherein:
the quantum well layers and the barrier layers have associated thicknesses,
an amount of silicon doping, a spacing of quantum wells in the quantum well layers, and the thicknesses of the quantum well layers and the barrier layers are selected for the QWIPs to tune the QWIPs to have a limited spectral bandwidth with a peak response within a wavelength range of 10.4 μm to 10.8 μm corresponding to at least a portion of an infrared absorption band of the one or more gasses and to have a full width half maximum spectral bandwidth of less than 0.7 μm in response to the radiation; and selecting an optical band pass filter adapted to be positioned substantially between the lens and the focal plane array and filter the infrared radiation to a wavelength range substantially corresponding to the limited spectral bandwidth of the QWIPs before the infrared radiation is received by the focal plane array, wherein the less than 0.7 μm spectral bandwidth of the focal plane array is selected to reduce signal noise substantially outside the wavelength range of 10.4 μm to 10.8 μm and dark current associated with at least the optical band pass filter and the focal plane array.

11. The method of claim 10, wherein:

the focal plane array is adapted to provide a plurality of signals in response to the filtered infrared radiation;
the less than 0.7 μm spectral bandwidth of the focal plane array is selected to reduce dark current associated with the optical band pass filter and/or the focal plane array; and
the method comprising providing a processor adapted to render an image of the one or more gasses in response to the signals.

12. The method of claim 11, comprising providing an output port adapted to pass the image to an external device.

13. The method of claim 11, comprising providing a display adapted to provide the image to a user for viewing.

14. The method of claim 10, wherein the lens is adapted to focus the infrared radiation at a focal plane substantially coincident with the focal plane array.

15. The method of claim 10, wherein the limited spectral bandwidth of the infrared radiation is longwave infrared radiation.

16. The method of claim 10, wherein the one or more gasses include a gas leak plume.

17. The method of claim 10, wherein the one or more gasses include a gas identified in TABLE 2.

18. The method of claim 10, further comprising using the infrared camera system to detect gasses absorbing infrared radiation in the wavelength range of 10.4 to 10.8 μm.

19. A method of operating the infrared camera system of claim 5 to detect the one or more gasses, the method comprising:

positioning the infrared camera system to receive the infrared radiation from the survey scene through the lens;
using the infrared camera system to render and display the image of the one or more gasses; and
viewing the image on the display to determine a presence of the one or more gasses.

* * * * *